US008106040B2

(12) United States Patent
Gao et al.

(10) Patent No.: US 8,106,040 B2
(45) Date of Patent: Jan. 31, 2012

(54) STABILIZING COMPOSITIONS FOR ANTIBIOTICS AND METHODS OF USE

(75) Inventors: Shen Gao, Bolton (CA); Daniel A. Moros, Larchmont, NY (US); Satish Asotra, Brampton (CA)

(73) Assignee: Taro Pharmaceuticals North America, Inc., Grand Cayman (KY)

( * ) Notice: Subject to any disclaimer, the term of this patent is extended or adjusted under 35 U.S.C. 154(b) by 0 days.

(21) Appl. No.: 11/902,925

(22) Filed: Sep. 26, 2007

(65) Prior Publication Data

US 2008/0076749 A1    Mar. 27, 2008

Related U.S. Application Data

(60) Provisional application No. 60/847,093, filed on Sep. 26, 2006.

(51) Int. Cl.
*A61K 31/43* (2006.01)
*A61K 31/545* (2006.01)
*A61K 31/424* (2006.01)
(52) U.S. Cl. .............. 514/192; 514/200; 514/210.06
(58) Field of Classification Search ............... 514/192
See application file for complete search history.

(56) References Cited

U.S. PATENT DOCUMENTS

| | | | |
|---|---|---|---|
| 3,402,843 A | 9/1968 | Campbell | |
| 3,636,194 A | 1/1972 | Parizeau | |
| 3,912,100 A | 10/1975 | Graham et al. | |
| 3,996,355 A * | 12/1976 | Lin et al. .............. | 514/86 |
| 4,079,132 A | 3/1978 | Lin et al. | |
| 4,172,138 A | 10/1979 | Rhodes | |
| 4,282,202 A | 8/1981 | Dowrick et al. | |
| 4,684,643 A | 8/1987 | Buddenbaum et al. | |
| 4,734,304 A | 3/1988 | Tsubone et al. | |
| 4,918,108 A | 4/1990 | Kern et al. | |
| 5,795,902 A | 8/1998 | Ahmed | |
| 6,177,421 B1 * | 1/2001 | Moir et al. .............. | 514/197 |
| 6,608,223 B2 * | 8/2003 | Rao et al. .............. | 554/169 |
| 6,977,086 B1 * | 12/2005 | Barges et al. .............. | 424/489 |
| 7,276,468 B1 | 10/2007 | Tucker | |
| 2004/0202696 A1 | 10/2004 | Yamin et al. | |
| 2005/0287180 A1 * | 12/2005 | Chen .............. | 424/400 |
| 2006/0177414 A1 | 8/2006 | Mertin et al. | |
| 2007/0184101 A1 | 8/2007 | Hrakovsky et al. | |
| 2008/0069882 A1 | 3/2008 | Dietrich et al. | |

FOREIGN PATENT DOCUMENTS

| | | |
|---|---|---|
| EP | 0 115 001 | 8/1984 |
| FR | 2 186 230 | 8/1972 |
| FR | 2 374 031 | 12/1977 |
| GB | 654 215 | 6/1951 |
| GB | 767 153 | 1/1957 |
| GB | 1 372 102 | 10/1974 |
| JP | 06 345879 | 12/1994 |
| JP | 09 058687 | 7/1997 |
| WO | WO 98/50019 A1 | 11/1998 |
| WO | WO 01/28555 A1 | 4/2001 |
| WO | WO/01/85568 | 11/2001 |
| WO | WO 2004/093875 A1 | 11/2004 |
| WO | WO2005/077342 A1 | 8/2005 |
| WO | WO 2008/039472 | 4/2008 |

OTHER PUBLICATIONS

Wildfeuer et al. Arzneimittelforschung 41(1):70-73 (1991). (Submitted with English-language abstract from http://www.ncbi.nlm.nih.gov/pubmed/2049115?ordinalpos=1&itool=EntrezSystem2.PEntrez.Pubmed.Pubmed_ResultsPanel.Pubmed_RVDocSum, printed on Feb. 27, 2008).
Deshpande et. al, "Degradation of β-lactam Antibiotics", Current Science, 87:12 1684-1695 (2004).
Naas et al., "Integration of a Transposon Tn1-Encoded Inhibitor-Resistant β-Lactamase Gene, $bla_{TEM-67}$ from *Proteus mirabilis*, into the *Escherichia coli* Chromosome", Antimicrobial Agents and Chemotherapy, 47:1 p. 19-26, (2003).
Ueda et al., "Effect of Ethyl Cellulose in a Medium-Chain Triglyceride on the Bioavailability of Ceftizoxime", J Pharm Sci. 72(4):454-8 (1983).
Berman et al., "Otitis media-related antibiotic prescribing patterns, outcomes, and expenditures in a pediatric medicaid population", Pediatrics, 100, No. 4 (Oct. 1997), pp. 585-592.
Glasziou et al., "Antibiotics for acute otitis media in children", Cochrane Database Syst Rev. (2):CD000219 (2000).
Hoizey et al., J Pharm Biomed Anal. 15;30(3):661-6 (2002).
Choi et al., J Pharm Biomed Anal. 1;35(1):221-31 (2004).
"Amoxicillin", USP 27, *Official Monographs*, p. 138-142.
"Amoxicillin and Clavulanate Potassium", USP 27, *Official Monographs*, p. 142-143.
"Clavulanate Potassium", USP 27, *Official Monographs*, p. 464-465.
Moore et al., "Stability of Amoxicillin-Clavulanate in BACTEC Medium Determined by High-Performance Liquid Chromatography and Bioassay", Journal of Clinical Microbiology, vol. 34, No. 5, May 1996, p. 1321-1322.
"Medium Chain Triglycerides", *Handbook of Pharmaceutical Excipients*, 5th ed., edited by R. Rowe et al., p. 454-456.
Mandell and Petri, "Antimicrobial Agents (Continued): Penicillins, Cephalosporins, and Other β-Lactam Antibiotics", Goodman and Gilman's, The Pharmacological Basis of Therapeutics, Ninth Ed., 1996, ch. 45.
"Otitis media (Ear Infection)", National Institute on Deafness and Other Communication Disorders, http://www.nidcd.nih.gov/health/hearing/otitism.asp, p. 1-7, last accessed Feb. 6, 2008.
Wardrop et al., "Multiple-layer compression-coated tablets: formulation and humidity studies of novel chewable amoxicillin/clavulanate tablet formulations," Drug Dev Ind Pharm. Aug. 1998, 24(8): 729-736.

(Continued)

*Primary Examiner* — Sreeni Padmanabhan
*Assistant Examiner* — Timothy E Betton
(74) *Attorney, Agent, or Firm* — Venable LLP; Michael A. Gollin; Thomas F. Barry

(57) ABSTRACT

The present invention is directed to improved liquid antibiotic formulations. In some embodiments, the present invention is directed to a composition comprising an antibiotic in a liquid comprising triglycerides, wherein the composition has less than about 5% water (w/v).

27 Claims, 2 Drawing Sheets

OTHER PUBLICATIONS

Mehta et al., "Stability of amoxicillin and potassium clavulanate in amoxiclav oral suspension", J Clin Pharm Ther. Oct. 1994, 19(5): 313-315.

Reading et al., "The beta-lactamase stability of amoxicillin with the beta-lactamase inhibitor, clavulanic acid", J Antimicrob Chemother., Jan. 1983, 11(1): 27-32.

Ekstrom, B. "Basic design of beta-lactam antibiotics: penams and analogues and monocyclic beta-lactams", Scand J Infect Dis Suppl. 1984; 42: 38-49.

Fuchs et al., "Disk diffusion susceptibility testing of ticarcillin plus clavulanic acid", J Clin Micrbiol. 1984, 19(4): 555-557.

Kenig MD, "Spectrophotometric determination of the stability of clavulanic acid and its ether and amine derivatives in serum and urine", Analyst. May 1988, 113(5): 761-764.

Goodman and Gilman's, The Pharmacological Basis of Therapeutics, Ninth Ed., 1996, ch. 46.

Remington: The Science and Practice of Phamacy, 21$^{st}$ Ed. (2006), pp. 1633-1641.

Alsarra; Development of a stability-indicating HPLC method for the determination of montelukast in tablets and human plasma and its applications to pharmacokinetic and stability studies; Saudi Pharmacology Journal 2004, 12(4): 136-143.

Caliari et al.; Medium chain triglyceride absorption in patients with pancreatic insufficiency; Scandanavian Journal of Gastroenterology 1996, 31:90-94.

Diamant et al.; The effect of montelukast (MK-0476), a cysteinyl leukotriene receptor antagonist, on allergen-induced airway responses and sputum cell counts in asthma; Clinical and Experimental Allergy 1999, 29: 42-51.

European Search Report for EP 0 115 001 of Nov. 7, 1985.

ISR for PCT/EP01/05121, mailed Nov. 7, 2001.

ISR for PCT/US2007/020721, mailed Apr. 3, 2008.

Montelukast; DrugBank, www.drugbank.ca.

Remington: The Science and Practice of Pharmacy 2006, 21st ed., table of contents.

Traul et al.; Review of the toxicologic properties of medium-chain triglycerides; Food and Chemical Toxicology 2000, 38: 79-98.

Office Action mailed on May 20, 2011 in U.S. Appl. No. 12/412,029.

Zhao, et al., "Pharmacokinetics and Bioavailability of Montelukast Sodium (MK-0476) in Healthy Young and Elderly Volunteers," *Biopharmaceutics & Drug Disposition*, vol. 18:9, pp. 769-777 (1997).

International Search Report and Written Opinion mailed Nov. 9, 2009 in International App. No. PCT/US2009/038435.

Office Action mailed Sep. 27, 2011 in U.S. Appl. No. 12/412,029.

* cited by examiner

| No. | Ingredient | Amount for 100g |
|---|---|---|
| 1 | Amoxicillin trihydrate | 3.05 |
| 2 | Potassium clavulanate / silicon dioxide (1:1 blend) | 1.66 |
| 3 | Silicon dioxide 63FP | 1.05 |
| 4 | Colloidal silicon dioxide | 0.05 |
| 5 | Medium chain triglycerides (Myritol 318PH) | 93.98 |
| 6 | Sorbitan monostearate | 0.2 |
| 7 | Butylated hydroxytoluene (BHT) | 0.01 |

Fig. 1B

| No. | Ingredient | Amount for 100g |
|---|---|---|
| 1 | Amoxicillin trihydrate | 3.05 |
| 2 | Potassium clavulanate / silicon dioxide (1:1 blend) | 1.66 |
| 3 | Silicon dioxide 244FP | 1.05 |
| 4 | Colloidal silicon dioxide | 0.05 |
| 5 | Medium chain triglycerides (Myritol 318PH) | 93.98 |
| 6 | Sorbitan monostearate | 0.2 |
| 7 | Butylated hydroxytoluene (BHT) | 0.01 |

Fig. 1C

| No. | Ingredient | Amount for 100g |
|---|---|---|
| 1 | Amoxicillin trihydrate | 3.05 |
| 2 | Potassium clavulanate / silicon dioxide (1:1 blend) | 1.66 |
| 3 | Silicon dioxide 72FP | 1.05 |
| 4 | Colloidal silicon dioxide | 0.05 |
| 5 | Medium chain triglycerides (Myritol 318PH) | 93.98 |
| 6 | Sorbitan monostearate | 0.2 |
| 7 | Butylated hydroxytoluene (BHT) | 0.01 |

Fig. 1D

| No. | Ingredient | Amount for 50g |
|---|---|---|
| 1 | Amoxicillin trihydrate | 3.05 |
| 2 | Potassium clavulanate / silicon dioxide (1:1 blend) | 1.66 |
| 3 | Silicon dioxide 63FP | 0.525 |
| 4 | Colloidal silicon dioxide | 0.025 |
| 5 | Medium chain triglycerides (Myritol 318PH) | 47.00 |
| 6 | Sorbitan monostearate | 0.1 |
| 7 | Butylated hydroxyanisole (BHA) | 0.005 |
| 8 | Butylated hydroxytoluene (BHT) | 0.005 |

STABILIZING COMPOSITIONS FOR ANTIBIOTICS AND METHODS OF USE

FIELD OF THE INVENTION

The present invention is directed to improved liquid antibiotic formulations. In some embodiments, the present invention is directed to a composition comprising an antibiotic in a liquid comprising triglycerides, wherein the composition has less than about 5% water (w/v).

BACKGROUND OF THE INVENTION

β-lactam antibiotics are commonly prescribed antibiotics that are active against both gram-positive and gram-negative organisms. See Goodman and Gilman's, The Pharmacological Basis of Therapeutics, Ninth Ed., 1996 (Goodman and Gilman's). Penicillins include penicillins G and V which are active against gram-positive cocci, naficillin which is active against penicillinase-producing Staphylococcus aureus and ampicillin which has an improved gram-negative spectrum of activity. Unfortunately, bacterial resistance to β-lactam antibiotics is growing. A major mechanism of resistance involves the production of β-lactamases by the bacteria. β-lactamases cleave the β-lactam ring generating penicilloic acid, which is not bacteriocidal.

β-lactamases can be inhibited by molecules which bind to the β-lactamases, acting as competitive substrates for the enzymes. One such molecule, clavulanic acid, binds irreversibly to the β-lactamases, irreversibly inhibiting the enzyme. Clinically, the addition of β-lactamase inhibitors to penicillins is very important because it extends the spectrum of bacteriocidal activity. For example, the combination of amoxicillin and clavulanic acid is effective against the β-lactamase-producing strains of staphylococci, H. influenza, gonococci and E. coli. The addition of clavulanic acid to ticarcillin extends its bacteriocidal activity to include aerobic gram-negative bacilli, Staphylococcus aureus as well as Bacteroides species. Other β-lactamases inhibitors include, sulbactam and tazobactam.

Unfortunately, β-lactamase inhibitors such as clavulanic acid are unstable in aqueous media. U.S. Pat. No. 6,177,421. Clavulanic acid is susceptible to hydrolytic degradation. There exists a narrow range of pH and temperature where the molecule is most stable. Wildfeuer et al. Arzneimittelforschung 41(1):70-73 (1991).

Given the growth of antibiotic resistant bacteria and the importance of penicillins as a first-line therapy, there exists a continuing need to develop formulations containing β-lactamase inhibitors that are stable.

SUMMARY OF THE INVENTION

The present invention is directed to a composition comprising an antibiotic in a liquid comprising triglycerides, wherein the composition has less than about 5% water (w/v). In some embodiments, the antibiotic is selected from the group consisting of a penicillin, a cephalosporin, a carbapenem, and mixtures thereof. In some embodiments, the antibiotic is a penicillin selected from the group consisting of penicillin G, penicillin V, methicillin, nafcillin, oxacillin, cloxacillin, dicloaclin, ampicillin, amoxicillin, carbenicillin, ticarcillin, piperacillin, meziocillin, aziocillin, and mixtures thereof.

The triglycerides can be selected from the group consisting of short chain triglycerides, medium chain triglycerides, and long chain triglycerides. In some embodiments, the triglycerides are medium chain triglycerides.

In some embodiments, the triglycerides can be about 5% (w/v) to about 99% (w/v), about 25% (w/v) to about 99% (w/v), about 50% (w/v) to about 99% (w/v), about 75% (w/v) to about 99% (w/v), about 85% (w/v) to about 99% (w/v), or about 95% (w/v) to about 99% (w/v) of the composition.

In some embodiments, the composition has less than about 1% water (w/v), in another embodiment there is less than about 0.5% water (w/v), and in a third embodiment there is less than about 0.1% water (w/v). The composition can also be a dry triglyceride liquid formulation in some embodiments.

The composition of the present invention can further comprise a β-lactamase inhibitor, for example, clavulanic acid. In some embodiments, the compositions of the present invention comprise clavulanic acid, amoxicillin, and medium chain triglycerides.

The present invention is further directed to a composition comprising a penicillin and a β-lactamase inhibitor in a liquid comprising medium chain triglycerides, wherein the concentration of triglycerides ranges from about 5% (w/v) to about 95% (w/v), and wherein the composition has less than about 5% water (w/v). In some embodiments, the penicillin is amoxicillin and the β-lactamase inhibitor is clavulanic acid. In some embodiments, the concentration of amoxicillin ranges from about 50 mg/5 ml to about 800 mg/5 ml and clavulanic acid ranges from about 10 mg/5 ml to about 80 mg/5 ml.

The present invention is also directed to a composition comprising a penicillin and a β-lactamase inhibitor, wherein the penicillin and β-lactamase inhibitor are in a liquid comprising medium chain triglycerides, wherein the concentration of triglycerides can be about 70% (w/v) to about 99% (w/v).

In some embodiments, the penicillin or antibiotic is stable for at least about ten days when stored at a temperature of about 20° C. to about 25° C.

The present invention is also directed to kits comprising any embodiment of the compositions of the present invention. For example, the present invention is directed to a kit comprising a composition comprising an antibiotic which can be mixed with a liquid comprising triglycerides, wherein the composition has less than about 5% water (w/v). In some embodiments, the kit comprises (a) a first container comprising a therapeutically effective amount of an antibiotic and (b) a second container comprising a pharmaceutically acceptable carrier, excipient, diluent or combination thereof. In some embodiments, at least one container can be made of high density polyethylene.

The present invention is also directed to methods of using the compositions of the present invention. For example, the present invention is directed to a method of treating a microbial infection in a mammal, the method comprising administering a composition comprising an antibiotic in a liquid comprising triglycerides, wherein the composition has less than about 5% water (w/v) to the mammal in need thereof.

DESCRIPTION OF THE DRAWINGS

FIG. 1 (A, B, C, and D) illustrates exemplary embodiments of the present invention.

DETAILED DESCRIPTION

The headings below are provided solely for organizational purposes and are not intended to impart any division or meaning to this document, unless specifically indicated.

Compositions

The present invention is directed to compositions comprising an antibiotic compound in a liquid comprising triglycerides, wherein the composition has less than about 5% water (w/v). In some embodiments, the composition can further comprise a β-lactamase inhibitor. The antibiotic compound can be in suspension or in solution in the liquid comprising triglycerides.

The term "antibiotic" encompasses any pharmaceutically acceptable compound that can inhibit the growth of or destroy bacteria and/or other microbes, regardless of whether the compound is produced in a microorganism or produced synthetically. This term encompasses disinfectants, antiseptics, and any other antimicrobial compounds. For example, the term "antibiotic" encompasses penicillin and all its derivatives.

Suitable antibiotics for use in the present invention include, but are not limited to, the β-lactam class of antibiotics which comprises penicillins, cephalosporins, and carbapenems. β-lactam antibiotics are useful as antimicrobial agents. These compounds inhibit the synthesis of the bacterial peptidoglycan cell wall and are active against both gram-positive and gram-negative cell walls.

Penicillins can be generally classified based on their spectrum of microbial activity. Penicillin G and penicillin V are highly active against strains of gram-positive cocci. However, these drugs are readily hydrolyzed by penicillinase making them ineffective against most strains of *Staphylococcus aureus*. In some embodiments, the antibiotic of the present invention is penicillin G, penicillin V, or a mixture thereof.

Penicillinase-resistant penicillins tend to have less potent antimicrobial activity against microbes sensitive to penicillin G but these penicillins are active against *Staphylococcus aureus*. Exemplary penicillinase-resistant penicillins include, but are not limited to, methicillin, nafcillin, oxacillin, cloxacillin, and dicloxacillin. In some embodiments, the antibiotic of the present invention is methicillin, nafcillin, oxacillin, cloxacillin, dicloxacillin, or a mixture thereof.

Another group of penicillins include those whose spectrum of antimicrobial activity extends to include gram-negative organisms such as *Haemophilus influenza, E. coli*, and *Proteus mirabilis*. However, these drugs are hydrolyzed by β-lactamases that are found in increasing numbers of gram-negative bacteria. In some embodiments, the antibiotic of the present invention is ampicillin, amoxicillin, bacampicillin, or a mixture thereof.

Still other penicillins, such as, carbenicillin, carbenicillin indanyl, and ticarcillin are classified together because their spectrum of antimicrobial activity includes *Pseudomonas, Enterobacter*, and *Proteus* species. Other extended-spectrum penicillins include mezlocillin and piperacillin, which have activity against *Pseudomonas, Klebsiella*, and other gram-negative microbes. However, these drugs are also hydrolyzed by β-lactamases. In some embodiments, the antibiotic of the present invention is carbenicillin, carbenicillin indanyl, ticarcillin, mezlocillin, piperacillin, or a mixture thereof.

The present invention is also directed to using cephalosporins. Cephalosporins can be categorized depending on their generation, as described in Goodman and Gilman's. First generation cephalosporins include cephalothin, cefazolin, cephalexin, and cefadroxil. Second generation cephalosporins include cefamandole, cefoxitin, cefaclor, cefuroxime, cefuroxime axetil, loracarbef, cefonicid, cefotetan, and ceforamide. Third generation cephalosporins include cefoxatime, cefopodoxime proxetil, cefizoxime, cefoperazone, and ceftazidime. Finally, an exemplary fourth generation cephalosporin is cefepime.

In some embodiments, the antibiotic of the present invention is cephalothin, cefazolin, cephalexin, cefadroxil, cefamandole, cefoxitin, cefaclor, cefuroxime, cefuroxime axetil, loracarbef, cefonicid, cefotetan, ceforamide, cefoxatime, cefopodoxime proxetil, cefizoxime, cefoperazone, ceftazidime, cefepime, or a mixture thereof.

The present invention is further directed to using β-lactam antibiotics other than penicillins or cephalosporins. These other β-lactam antibiotics include those compounds that have a β-lactam structure but are not considered a penicillin or cephalosporin. For example, the carbapenems which include imipenem, meropenem, and aztreonam. In some embodiments, the antibiotic of the present invention is imipenem, meropenem, aztreonam, or a mixture thereof. As one of skill in the art will appreciate, the above list of antibiotics is not exhaustive and other antibiotics which are not mentioned are also encompassed within the present invention.

In some embodiments, the compositions of the present invention can comprise more than one antibiotic. For example, the present invention is also directed to a composition comprising more than one antibiotic in a liquid comprising triglycerides, wherein the composition has less than about 5% water (w/v). In some embodiments, the present invention comprises 2, 3, 4, or 5 or more antibiotics in combination. The antibiotics used in the embodiments of the present invention that comprise more than one antibiotic can be selected from a group consisting of, but not limited to, a penicillin, a cephalosporin, a carbapenem, or a mixture thereof.

The embodiments of the present invention that include more than one antibiotic can be useful for treating mammals with an infection from more than one bacteria or other microbe. For example, a physician may prescribe a penicillin such as carbenicillin to treat an infection caused by *Pseudomonas* and a second antibiotic to treat an infection caused by a different microbe that carbenicillin cannot treat.

The above β-lactam antibiotics are susceptible to inactivation by β-lactamase. The β-lactamase enzyme opens the β-lactam ring in penicillin or other β-lactam antibiotics. This change produces penicillonic acid (from penicillins) and eliminates the antibiotic properties of penicillin. Similar attacks reduce the ability of other β-lactam antibiotics to treat microbe caused diseases. See Despande et. al, Degradation of β-lactam Antibiotics, Current Science, 87:12 1684-1695 (2004).

This presents a problem for treating those bacteria and other microbes that have the ability to produce β-lactamase as a defense mechanism. For example, if a physician administers a β-lactam antibiotic to treat microbes that produce β-lactamase, the therapeutic effect of the antibiotic with be reduced or there will be no effect.

To overcome this problem, the antibiotic can be administered in combination with a β-lactamase inhibitor. A "β-lactamase inhibitor" is a compound that can bind β-lactamase thereby preventing it from inactivating the antibiotic. As one of skill in the art will appreciate, this term encompasses all forms of the compound including, for example, acids, bases, salts, and esters thereof, as well as polymorph crystal forms. In some embodiments, a "β-lactamase inhibitor" refers to a pharmaceutically acceptable salts selected from, but not limited to, alkali metal salts such as sodium or potassium, alkaline earth salts or an ammonium salt (all of which are herein referred to as a pharmaceutically acceptable salts).

In some embodiments, the compositions of the present invention further comprise a β-lactamase inhibitor. The β-lactamase inhibitor can be clavulanic acid, sulbactam, tazobactam, or mixtures thereof, as well as the salts and esters of these compounds. In some embodiments, the β-lactamase inhibitor is potassium clavulanate.

These β-lactamase inhibitors are often prescribed in association with amino- and ureidopenicillins for treating gram-negative infections. See Naas et al., Integration of a Transposon Tn1-Encoded Inhibitor-Resistant 3-Lactamase Gene, bla$_{TEM-67}$ from *Proteus mirabilis*, into the *Escherichia coli* Chromosome, Antimicrobial Agents and Chemotherapy, 47:1 p. 19-26, (2003). For example, clavulanic acid has been combined with amoxicillin to form an oral preparation (AUGMENTIN®, available from GlaxoSmithKline, Research Triangle Park, N.C.) and with tiarcillin as a parenteral preparation (TIMENTIN®, available from GlaxoSmithKline, Research Triangle Park, N.C.).

These products suffer from poor stability because of the water content of their formulations. This is a major problem for clavulanic acid and its salts because they are extremely sensitive to the presence of water and undergo rapid hydrolytic degradation, both as a dry-powder and in a reconstituted state. In particular, in aqueous solutions, clavulanic acid is unstable and beaks down reducing the amount available to bind β-lactamases.

For example, when amoxicillin and clavulanic acid are used together, the mixture can be reconstituted in water before it is administered to a patient. Even when stored at 4° C., the clavulanic acid degrades rapidly, reducing its effectiveness.

In some embodiments, the compositions of the present invention comprise less than 90%, 80%, 70%, 60%, 50%, 40%, 30%, 20%, or 10% water (w/v). The present invention can also comprise less than 5%, 4%, 3%, 2%, 1%, 0.1%, 0.01% (w/v) or be completely free of water. These low water embodiments can be used with water labile components, for example, clavulanic acid.

According to the present invention, surprisingly, the addition of triglycerides to a liquid suspension containing an antibiotic, e.g. a β-lactam, and a β-lactamase inhibitor, e.g. clavulanic acid, prevents degradation of the clavulanic acid.

Triglycerides (also known as triacylglycerol or triacylglyceride) are glycerides in which the glycerol is esterified with three fatty acids. Triglycerides are the main constituent of vegetable oil and animal fats. The general chemical structure of triglycerides is shown below:

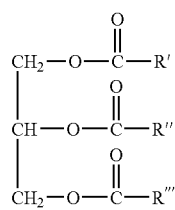

R', R", and R''' are alkyl chains ($C_1$-$C_n$).

Chain lengths of the fatty acids in naturally occurring triglycerides may range from 3 to 24 carbon atoms, but lengths of 16 and 18 carbon atoms are most common. Shorter chain lengths may be found in some substances (butyric acid in butter). Most naturally occurring fats contain a complex mixture of individual triglycerides. Based on their chain length, triglycerides can be divided into three categories: (i) short chain triglycerides (SCT); (ii) medium chain triglycerides (MCT); and (iii) long chain triglycerides (LCT).

Short chain triglycerides are triglycerides having short chain fatty acids, e.g., $C_2$-$C_6$. For example, one short chain triglyceride is glyceryl tributyrate.

Medium chain triglycerides have fatty acids ranging from about $C_8$ to about $C_{10}$. Some exemplary commercially available medium chain triglycerides are LABRAFAC® (available from Gattefossé Pharina, Saint-Priest Cedex, France) CAPTEX® (available from Parchem, White Plains, N.Y.), NESATOL® (available from Kreglinger Europe, Antwerp, Belgium) WAGLINOL® (available from Industrial Quimica Lasem, S.A., Barcelona, Spain), BERGABEST® (available from Sternchemie, Hamburg, Germany), MIGLYOL® (available from Universal Preserv-A-Chem, Inc., Edison, N.J.), NEOBEE® (available from Stepan Company, Northfield, Ill.), and CRODAMOL® (available from Croda, Edison, N.J.).

Triglycerides longer than a medium chain triglyceride, e.g. $C_{11}$ to $C_x$ are called long chain triglycerides. One exemplary long chain triglyceride is castor oil.

The compositions of the present invention can comprise a short chain, medium chain, or long chain triglyceride. In some embodiments, the triglyceride is a medium chain triglyceride. In some embodiments of the present invention, the use of a medium chain triglyceride can increase the bioavailability of a drug. See Ueda et al., Effect of Ethyl Cellulose in a Medium-Chain Triglyceride on the Bioavailability of Ceftizoxime, J Pharm Sci. 72(4):454-8 (1983).

The present invention can also comprise a mixture of triglycerides. In some embodiments, the mixture of triglycerides comprises a mixture of a short chain and a medium chain, a short chain and a long chain, or a medium chain and a long chain. Further, the mixture of triglycerides can comprise more than one short chain, more than one medium chain, or more than one long chain.

The compositions of the present invention can comprise about 1% to about 99% triglycerides (w/v). In some embodiments, the inactive components of the present invention comprise about 1% to about 25%, about 25% to about 50%, about 50% to about 75%, or about 75% to about 100% triglycerides (w/v). In some embodiments, the composition comprises about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5% of triglycerides (w/v). The term "about" refers to plus or minus 10% of the indicated number. For example, "about 10%" indicates a range of 9% to 11%.

In some embodiments, the triglycerides are selected from the group consisting of, but not limited to, vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof.

In some embodiments, the triglycerides can be almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate;

glyceryl tricaprylate/caprate; glyceryl tricaprylate/caprate/laurate; glyceryl tricaprylate/caprate/linoleate; and glyceryl tricaprylate/caprate/stearate.

In addition to triglycerides, the compositions of the present invention can further comprise stabilizing agents. A "stabilizing agent" is a compound that can prevent or slow the degradation of the antibiotic or β-lactamase inhibitor while in storage.

In some embodiments, the compositions of the present invention are stable for at least about ten days when stored at a temperature of about 20° C. to about 25° C. In some embodiments, the compositions of the present invention are stable for about ten days to about 31 days when stored at a temperature of about 20° C. to about 25° C.

That is, the compositions of the present invention are stable at a temperature of about 20° C. to about 25° C. during a course of antibiotic treatment. In some embodiments, the compositions of the present invention do not require refrigeration during a course of antibiotic treatment. A course of antibiotic treatment can be, but is not limited to, about 1, about 3, about 5, about 7, about 10 days, or about 31 days. Further a course of antibiotic treatment can be as long as the antibiotics are prescribed for use by a medical professional authorized to prescribe antibiotics. This can length can be determined based on the needs and characteristics of the individual patient. For example, if the patient is immunosuppressed or immunocompromised then the course of antibiotic treatment can be longer than a week, a month, or a year, depending on the patient's condition.

The present invention can further comprise a pharmaceutically acceptable excipient other than the triglycerides previously mentioned. An "excipient" refers to a substance that is used in the formulation of pharmaceutical compositions, and, by itself, generally has little or no therapeutic value. Various excipients can be used in the invention, including those described in Remington: The Science and Practice of Pharmacy, 21$^{st}$ Ed. (2006). Excipients include, but are not limited to, antioxidants, anti-bacterial agents that prevent the decay of the formulation itself as opposed to those exhibiting a therapeutic effect, preservatives, chelating agents, buffering agents, agents for adjusting toxicity, colorings, flavorings and diluting agents, emulsifying and suspending agents, and other substances with pharmaceutical applications.

The term "pharmaceutically acceptable" excipient refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In some embodiments, the term "pharmaceutically acceptable" means approved by a regulatory agency of the Federal or a state government or listed in the U.S. Pharmacopoeia or other generally recognized international pharmacopoeia for use in animals, and more particularly in humans. In some embodiments, the excipients used in the compositions of the present invention are pharmaceutically acceptable.

In some embodiments, at least one of the excipients included in the liquid formulation can be further dried to reduce its moisture content. In some embodiments, the formulation uses dried silicon dioxide, colloidal silicon dioxide, magnesium trisilicate, or combinations of these excipients. The drying can be done using any method known to one of skill in the art, for example, by placing the excipient in a 105° C. oven overnight.

The dried excipients can be combined with low moisture content medium chain triglycerides (e.g., a moisture content of about 0.0275% w/w). For example, dried silicon dioxide, dried colloidal silicon dioxide and dried magnesium trisilicate and low moisture medium chain triglyceride oil (e.g. 0.0275%, w/w) can be used as part of a low moisture liquid formulation suitable for delivering an active ingredient, such as an antibiotic.

Some embodiments of the present invention are directed to dry or dehydrated triglyceride liquid formulations comprising an antibiotic. The terms "dry triglyceride liquid formulations" or "dehydrated triglyceride liquid formulations" both refer to pharmaceutical formulations comprising a triglyceride that are substantially free, and in some cases totally free, of water, and can be considered to be dehydrated. These formulations can also be considered anhydrous. Such formulations can be prepared using low moisture content medium chain triglycerides and powdered excipients with low moisture contents. The powdered excipients can be further dried to reduce their moisture content. As is evident, the term "dry" is used in relation to a liquid to mean that the liquid and its contents have a low or a reduced water content. This use of the term "dry" is not intended to mean the liquid is devoid of fluid-like characteristics, e.g., it has become a powder.

The dry triglyceride liquid formulations of present invention are particularly useful in preventing hydrolytic degradation of clauvanic acid and/or potassium clauvanate when they are in a reconstituted antibiotic formulation. While not wishing to be bound to a single theory, the drying or desiccation of the excipients is believed to maximize their hygroscopic behavior in the reconstituted formulation. For example, silicon dioxide is very hygroscopic and adsorbs large quantities of water up to 30% (w/w) with a relative humidity of around 80% (w/w). This adsorptive ability is impaired if the silicon dioxide is exposed to humidity or other water before it becomes part of the reconstituted formulation. However, in its dried form, it is believed to adsorb water from within the formulation, which reduces the hydrolytic degradation of clauvanic acid and/or potassium clauvanate when they are in a reconstituted antibiotic formulation.

Methods of Treating

The compositions of the present invention can be administered to any mammal in need of the composition that can experience the beneficial effects of the compounds of the invention. Such mammals include humans and non-humans, such as pets and farm animals. Accordingly, the present invention is directed to methods of treating a microbial infection in a mammal, the method comprising administering a composition comprising an antibiotic in a liquid comprising triglycerides, wherein the composition has less than about 5% water (w/v), to the mammal in need thereof.

Various patients can find utility in the present invention. In some embodiments, the patient is a child. In some embodiments, the patient is about 55 years of age or older. In some embodiments, the patient has a bacterial infection. In some embodiments, the patient has a condition that compromises their immune system, e.g., AIDS or advanced stage cancer.

The dosage of the antibiotic administered will be dependent upon the age, health, and weight of the recipient, kind of concurrent treatment, if any, the frequency of treatment, and the nature of the effect desired. The compositions of the present invention can contain a quantity of a compound(s) according to this invention in an amount effective to treat the condition, disorder or disease of the subject being treated. One of ordinary skill in the art will appreciate that a method of administering pharmaceutically effective amounts of the antibiotic to a patient in need thereof can be determined empirically, or by standards currently recognized in the medical arts. It will be understood that, when administered to, for example, a human patient, the total daily dosage of the agents of the compositions of the present invention will be decided within the scope of sound medical judgment by the attending physician.

The specific therapeutically effective dose level for any particular patient will depend upon a variety of factors: the type and degree of the cellular response to be achieved; activity of the specific agent or composition employed; the specific agents or composition employed; the age, body weight, general health, gender and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

In some embodiments, the compositions of the present invention can be administered in combination with another therapeutic agent. Accordingly, the compositions of the present invention can also include one or more additional therapeutic agents such as, but not limited to, hydrophilic drugs, hydrophobic drugs, hydrophilic macromolecules, cytokines, peptidomimetics, peptides, proteins, toxoids, sera, antibodies, vaccines, nucleosides, nucleotides, nucleoside analogs, genetic materials and/or combinations thereof.

Additional examples of therapeutic agents that can be used in the pharmaceutical compositions of the present invention include, but are not limited to, other antineoplastic agents, analgesics and anti-inflammatory agents, anti-anginal agents, antihelmintics, anti-arrhythmic agents, anti-arthritic agents, anti-asthma agents, anti-viral agents, anti-coagulants, anti-depressants, antidiabetic agents, anti-epileptic agents, anti-emetics, anti-fungal agents, anti-gout agents, anti-hypertensive agents, anti-malarial agents, antimigraine agents, anti-muscarinic agents, anti-Parkinson's agents, anti-protozoal agents, anti-thyroid agents, thyroid therapeutic agents, antitussives, anxiolytic agents, hypnotic agents, neuroleptic agents, beta-blockers, cardiac inotropic agents, corticosteroids, diuretics, gastrointestinal agents, histamine $H_2$-receptors antagonists, immunosuppressants, keratolytics, lipid regulating agents, muscle relaxants, nutritional agents, cytokines, peptidomimetics, peptides, proteins, toxoids, sera, sedatives, sex hormones, sex hormone antagonists or agonists, stimulants antibodies, vaccines, nucleosides, nucleoside analogs and genetic materials. Amphiphilic therapeutic agents and nutritional agents can also be included.

The terms "treat" and "treatment" refer to both therapeutic treatment and prophylactic or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilization (i.e., not worsening) of the state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment. In some embodiments, the present invention is directed to a method of treating a microbial infection in a mammal, the method comprising administering a composition comprising an antibiotic in a liquid comprising triglycerides, to the mammal in need thereof.

A "pharmaceutically effective amount" means an amount effective to provide a therapeutic effect during a period of treatment. The effect can be the treatment of a bacterial infection or other microbe-caused disease state or condition. In some embodiments, the present infection is directed to a pharmaceutically effective amount of an antibiotic is administered to a mammal in need thereof.

As discussed previously, the methods and compositions of the present invention can be used to treat microbial caused diseases. In some embodiments, the methods and compositions of the present invention can be used to treat otitis media. Otitis media is an infection or inflammation of the middle ear caused by viral or bacterial infections. It is estimated that 75% of children experience at least one episode of otitis media by their third birthday, however, this infection is not limited to children. Otitis media can be treated using antibiotics. See Berman et al., Otitis media-related antibiotic prescribing patterns, outcomes, and expenditures in a pediatric medicaid population, Pediatrics, 102(1 Pt 1):157 (1998); Glasziou et al., Antibiotics for acute otitis media in children, Cochr ane Database Syst Rev. (2):CD000219 (2000). Thus, in some embodiments, the compositions of the present invention can be administered to a patient with otitis media to treat the infection.

Kits

The present invention is also directed to kits comprising a composition of the present invention. In some embodiments, the kits of the present invention further comprise a container or other means for holding the compositions of the present invention. In some embodiments, there is one container, two containers, three containers, or more than three containers.

Traditional aqueous based antibiotic formulations can be prepared at the pharmacy by mixing a measured amount of the powdered components with water. These formulations require refrigeration after mixing.

The kits of the present invention can be used to prepare the pharmaceutical compositions in a manner distinct from traditional kits. The medium chain triglycerides can be in a container separate from the powdered components, which can be in their own distinct container. The powdered components can comprise an antibiotic and clavulanic acid, or another β-lactamase inhibitor, either together or in separate containers. This allows the pharmacist to either pour the powders into the container with the liquid or vice versa. Storing the liquid and powder components in separate containers within a kit helps keep all the formulary components moisture-free because each container is only opened at the time of reconstitution, limiting the exposure to moisture in the environment.

Thus, in some embodiments, the kit comprises (a) a first container or other means for containing a therapeutically effective amount of the composition of the present invention and (b) a second container or other means for containing a pharmaceutically acceptable carrier, excipient, diluent or combination thereof. For example, the powdered portion of the formulation is stored in one container while the liquid is stored in a separate container. Optionally, the kit can have additional containers or other means for containing comprising a therapeutically effective amount of additional agents or excipients.

In some embodiments, the kit comprises a container or other means for containing for the separate compositions, such as, a divided bottle or a divided foil packet, however, the separate compositions can also be contained within a single, undivided container. Typically, the kit contains directions for administration of the separate components. The kit form is particularly advantageous when the separate components are preferably administered at different dosage intervals, or when titration of the individual components of the combination is desired by the prescribing physician.

In some embodiments, the antibiotic is in one container or other means for containing and the triglycerides are in another. The physician or pharmacist can then mix the two components to form a composition comprising an antibiotic in a liquid comprising triglycerides, wherein the composition has less than about 5% water (w/v). Any powdered excipients desired for the formulation can be present with the triglycerides (e.g., in a solution or a suspension) or they can be in a mixture with the antibiotic. The β-lactamase inhibitor may be in a container with the antibiotic or separate from the antibiotic in another container with powder.

In some embodiments, the kit of the present invention can further comprise an additional container or means for containing comprising a therapeutically effective amount of an agent selected from the group consisting of hydrophilic drugs, hydrophobic drugs, hydrophilic macromolecules, cytokines, peptidomimetics, peptides, proteins, toxoids, sera, antibodies, vaccines, nucleosides, nucleotides, nucleoside and/or nucleotide analogs, genetic materials and combinations thereof.

In some embodiments, the container or other means for containing of the kit is a bottle. This bottle can be moisture-proof, including a moisture proof cap. It is also important to select a bottle that will not be permeable to the triglycerides of the present invention, in particular, to the medium chain triglycerides. Some polymers that are suitable for aqueous solutions would not be suitable for use in the kits of the present invention.

Suitable containers or other means for containing include, but are not limited to, bottles made of high density polyethylene (HDPE), polypropylene (PP), glass, and metal. HDPE bottles are particularly suited for the present invention because molecules of HDPE have fewer branches and side chains which leads to higher density and smaller pores. This makes it an effective barrier to contain medium chain triglycerides within the bottle as well as an effective barrier to prevent an influx of water. Accordingly, in some embodiments, the container is a HDPE bottle.

As one of skill in the art will appreciate, the container is not limited to HDPE bottles. Table 1 shows a comparison of the properties of some more bottles contemplated for use in the present invention.

TABLE 1

| Bottle | PET | PETG | HDPE | LDPE | PP |
|---|---|---|---|---|---|
| Moisture barrier | Fair to Good | Fair to Good | Good to Excellent | Good | Good to Excellent |
| Oxygen barrier | Good | Good | Poor | Poor | Poor |
| Clarity | Clear | Clear | Opaque | Opaque | Translucent |

A method according to the present invention comprises preparing a pharmaceutical composition by combining a dehydrated triglyceride with a powdered antibiotic and, optionally, a β-lactamase inhibitor such as clavulanic acid. Any of the kits of the present invention are useful in this method.

The following examples are further illustrative of the present invention, but are not to be construed to limit the scope of the present invention.

EXAMPLE 1

The compositions of the present invention have better stability than aqueous solutions containing clavulanic acid. To demonstrate this, samples of some embodiments of the present invention are prepared at potassium clavulanate concentrations of 15 mg/5 mL, 35 mg/5 mL and 90 mg/5 mL. Each sample is dispersed in a vehicle of medium chain triglycerides and water. Further, the above sample preparation is repeated with the addition of amoxicillin at 250 mg/5 mL. Table 2 shows the ratios of MCT:water that are used in each sample prepared.

TABLE 2

| MCT:Water | Potassium clavulanate | | |
|---|---|---|---|
| (Diluent) | 15 mg (Ratio ~17) | 35 mg (Ratio ~7) | 90 mg (Ratio ~3) |
| 1:3 (pH per USP between 3.8 to 6.6) | *No amoxicillin *Amoxicillin 250 mg/5 mL | *No amoxicillin *Amoxicillin 250 mg/5 mL | *No amoxicillin *Amoxicillin 250 mg/5 mL |
| 1:1 (pH per USP between 3.8 to 6.6) | *No amoxicillin *Amoxicillin 250 mg/5 mL | *No amoxicillin *Amoxicillin 250 mg/5 mL | *No amoxicillin *Amoxicillin 250 mg/5 mL |
| 3:1 (pH per USP between 3.8 to 6.6) | *No amoxicillin *Amoxicillin 250 mg/5 mL | *No amoxicillin *Amoxicillin 250 mg/5 mL | *No amoxicillin *Amoxicillin 250 mg/5 mL |
| 100% MCT | *No amoxicillin *Amoxicillin 250 mg/5 mL | *No amoxicillin *Amoxicillin 250 mg/5 mL | *No amoxicillin *Amoxicillin 250 mg/5 mL |

The pH of the samples is controlled so that the mixture of amoxicillin and potassium clavulanate have a pH of about 3.8 to about 6.6. Solutions of pure amoxicillin (2 mg/ml) have an optimum pH range of about 3.8 to about 6.0 and solutions of pure clavulanate potassium (1% solution) have an optimum pH range of about 3.8 to about 8.0.

These samples are stored at both a temperature of about 20° C. to about 25° C. and under refrigeration (about 4° C.) and are tested for pH and the amount of amoxicillin and clavulanate. The samples to be tested for pH and the amount of amoxicillin and clavulanate at the following time points: 0 day (day of reconstitution), 5 day, 10 day, 15 day, 1 month, 2 months and 3 months after reconstitution.

The pH is measured using any technique known to one of skill in the art. For example, using the methods described in the U.S. Pharmacopoeia.

The amount of amoxicillin and clavulanate are measured using HPLC or other assay capable of measuring the amount of amoxicillin and clavulanate. Quantification of the compounds by HPLC is used to determine the unknown concentration of both amoxicillin and clavulanate in the samples.

The samples are injected (about 10-20 μl) into a liquid chromatograph equipped with a 210-nm detector and a 4-mm×30-cm column that contains 3- to 10-μm packing L1. See U.S. Pharmacopoeia. The peaks of the sample are compared to the injection of a series of known concentrations of the standard compound solution (e.g., about 10 μl of amoxicillin and/or about 20 μl of clavulanate) onto the HPLC for detection. The chromatograph of these known concentrations gives a series of peaks that correlate to the concentration of the samples that are injected. The chromatogram is recorded and the responses for the major peaks are measured. One of skill in the art can then determine the percentage of clavulanate or amoxicillin in the solution using the methods described in the U.S. Pharmacopoeia or other equivalent method.

Further, for in vivo studies testing the stability of the samples, high-performance liquid chromatographic methods using ultraviolet detection at 220 nm can be used for the simultaneous determination of amoxicillin and clavulanic acid in human or dog plasma. See Hoizey et al., J Pharm Biomed Anal. 15; 30(3):661-6 (2002); Choi et al., J Pharm Biomed Anal. 1; 35(1):221-31 (2004).

As one of skill in the art will appreciate, the stability of the composition can be tested using methods other than HPLC. For example, bioassays and spectrophotometric methods could be used in place of HPLC or in addition to HPLC to determine the stability of the composition. Thus, testing using zone of inhibition assays, cell proliferation assays (e.g., using calorimetric dyes), and other equivalent methods are also encompassed by the present invention.

EXAMPLE 2

The formulations in FIG. 1A-D depict embodiments of the present invention. These formulations can be prepared by using the following exemplary methods.

The formulation depicted in FIG. 1A can be prepared by adding sorbitan monostearate and BHT to medium chain triglycerides to form a mixture, heating the mixture to 55° C., and then mixing the mixture until the components have dissolved. The resulting oil suspension is then cooled to a temperature of about 20° C. to about 25° C.

Next, the amoxicillin trihydrate, potassium clavulanate/silicon dioxide blend (1:1 blend), silicon dioxide (63FP), and colloidal silicon dioxide are weighed into the amounts listed in FIG. 1A and then mixed in a container, such as, a glass bottle to form a dry blend. The oil suspension is then added to the container. The container is shaken to suspend the dry blend in the oil suspension.

The formulation depicted in FIG. 1B can be prepared by adding sorbitan monostearate and BHT to medium chain triglycerides to form a mixture, heating the mixture to 55° C., and then mixing the mixture until the components have dissolved. The resulting oil suspension is then cooled to a temperature of about 20° C. to about 25° C.

Next, the amoxicillin trihydrate, potassium clavulanate/silicon dioxide blend (1:1 blend), silicon dioxide (244FP), and colloidal silicon dioxide are weighed into the amounts listed in FIG. 1B and then mixed in a container, such as, a glass bottle to form a dry blend. The oil suspension is then added to the container. The container is shaken to suspend the dry blend in the oil suspension.

The formulation depicted in FIG. 1C can be prepared by adding sorbitan monostearate and BHT to medium chain triglycerides to form a mixture, heating the mixture to 55° C., and then mixing the mixture until the components have dissolved. The resulting oil suspension is then cooled to a temperature of about 20° C. to about 25° C.

Next, the amoxicillin trihydrate, potassium clavulanate/silicon dioxide blend (1:1 blend), silicon dioxide (72FP), and colloidal silicon dioxide are weighed into the amounts listed in FIG. 1C and then mixed in a container, such as, a glass bottle to form a dry blend. The oil suspension is then added to the container. The container is shaken to suspend the dry blend in the oil suspension.

The formulation depicted in FIG. 1D can be prepared by adding sorbitan monostearate, BHA, and BHT to medium chain triglycerides to form a mixture, heating the mixture to 55° C., and then mixing the mixture until the components have dissolved. The resulting oil suspension is then cooled to a temperature of about 20° C. to about 25° C.

Next, the amoxicillin trihydrate, potassium clavulanate/silicon dioxide blend (1:1 blend), silicon dioxide (63FP), and colloidal silicon dioxide are weighed into the amounts listed in FIG. 1D and then mixed in a container, such as, a glass bottle to form a dry blend. The oil suspension is then added to the container. The container is shaken to suspend the dry blend in the oil suspension.

EXAMPLE 3

Reconstituted suspensions of the present invention, as listed in FIG. 1A-C and prepared according to Example 2, can be tested for stability at a temperature of about 20° C. to about 25° C. and compared to the brand product (Augmentin®) which is stored at about 4° C. The following data represents the observed results of this stability test.

TABLE 3

| Time point (days) | Formulation in FIG. 1A | Formulation in FIG. 1C | Formulation in FIG. 1B | Augmentin ® |
|---|---|---|---|---|
| 0 | Off-white to cream colored suspension, settles quickly | Off-white to cream colored suspension, settles less quickly than the formulation in FIG. 1A | Off-white to cream colored suspension, settles less quickly than the formulation in FIG. 1C | Cream colored viscous suspension. |
| 1 | Off-white to cream colored suspension, settles quickly | Off-white to cream colored suspension, settles less quickly than the formulation in FIG. 1A | Off-white to cream colored suspension, settles less quickly than the formulation in FIG. 1C | Cream colored viscous suspension. |
| 5 | Yellow colored suspension, settles quickly | Yellow colored suspension, settles less quickly than the formulation in FIG. 1A | Yellow colored suspension, settles less quickly than the formulation in FIG. 1C | Cream colored viscous suspension. |

EXAMPLE 4

The formulations described in FIG. 1A-C can be tested to determine the degradation of clavulanic acid and amoxicillin. These formulations can be prepared as described in Example 2 and then stored at a temperature of about 20° C. to about 25° C. The brand product (Augmenting®) can be prepared according to its labeling instructions and stored at a temperature of about 4° C. as the product labeling recommends.

At time points of 0 days (reconstitution of powder), 1 day, 5 days, and 8 days the following results were obtained using the HPLC methods described in the US Pharmacopoeia. Samples are withdrawn for assay from the top and bottom of the bottle to assess the homogeneity of the suspension.

TABLE 4

| Syloid Type (Silcon Gel) | Sample Info | Formulation in FIG. 1. | % Clav. | | | | % Amoxi. | | | |
|---|---|---|---|---|---|---|---|---|---|---|
| | | | 0 Day | 1 Day | 5 Day | 8 Day | 0 Day | 1 Day | 5 Day | 8 Day |
| 63FP | Sample 1-Bottom | FIG. 1A | 125.3 | 108.6 | 98.3 | 107.7 | 107.3 | 105.3 | 104.2 | 101.9 |
| | Sample 2-Top | FIG. 1A | 101.5 | 106.7 | 99.5 | 95.9 | 99.6 | 108.0 | 105.3 | 97.3 |
| 72FP | Sample 3-Bottom | FIG. 1C | 215.3 | 99.2 | 99.7 | 94.9 | 165.2 | 100.0 | 107.1 | 98.8 |
| | Sample 4-Top | FIG. 1C | 104.0 | 103.0 | 93.4 | 92.3 | 100.0 | 104.6 | 101.2 | 97.1 |
| 244FP | Sample 5-Bottom | FIG. 1B | 108.0 | 106.0 | 103.5 | 93.6 | 98.9 | 99.6 | 110.4 | 98.8 |
| | Sample 6-Top | FIG. 1B | 106.0 | 105.7 | 100.3 | 94.4 | 99.6 | 103.3 | 107.1 | 99.0 |
| NA | Augmentin ®-1Bottom | N/A | 112.5 | 113.4 | 103.3 | 97.7 | 101.0 | 111.0 | 104.3 | 98.1 |
| NA | Augmentin ®-2 Top | N/A | 115.7 | 112.9 | 103.2 | 97.5 | 103.0 | 110.0 | 104.6 | 98.5 |

As illustrated in Table 4, the sample containing 244FP (the formulation shown in FIG. 1B) had approximately 13% clavulanic acid degradation after 8 days at a temperature of about 20° C. to about 25° C. The brand product had approximately 15% clavulanic acid degradation after 8 days despite being stored at 4° C.

EXAMPLE 5

The inventors have also tested the formulation stability of formulations of the present invention which use pre-dried powdered excipients. For this test, part of the powdered components in the test formulation, including silicon dioxide, colloidal silicon dioxide and magnesium tricilicate, were dried in 105° C. oven overnight to reduce their water content. As a comparison, the samples (powders) of these materials from the same containers without drying were also studied.

Various medium chain triglyceride (MCT) oil samples with different moisture levels of 0.0275, 0.05, 0.1 and 0.15% (w/w) were evaluated for determining the stability of the formulation after reconstitution.

The stability of a formulation (600 mg/42.9 mg) was monitored using color change as an indicator of formulation stability. In general, the whiter the formulation appears, the more stable the formulation. It has been observed that for the formulations without pre-dried powders, the reconstituted suspension of the product became dark yellow on the second day after reconstitution, irrespective of the moisture level of MCT oil.

However, the formulations using pre-dried powders (silicon dioxide, colloidal silicon dioxide and magnesium trisilicate) did not show any color change for 3 days at all moisture levels of MCT oil after reconstitution. After 3 days following reconstitution, gradual color changes were observed in the formulations containing high moisture level MCT oil, whereas no color change or slight off-white was seen in 0.0275% MCT oil formulations for 21 days kept at room temperature (23±2° C.).

Similar observations were obtained on 200/28.5 mg formulation. The observation difference was the color change of the 200/28.5 mg formulations was faster than the 600/42.9 mg formulations. This may be attributed to the fact that the 200/28.5 mg formulation has far less amount of dry powders than the 600/42.9 mg formulation.

These examples illustrate possible embodiments of the present invention. As one of skill in the art will appreciate, because of the versatility of the compositions, kits, and methods of using the compositions disclosed herein, the compositions, kits, and methods can be used in other similar ways to those described herein. Thus, while the invention has been particularly shown and described with reference to some embodiments thereof, it will be understood by those skilled in the art that they have been presented by way of example only, and not limitation, and various changes in form and details can be made therein without departing from the spirit and scope of the invention. Therefore, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

We claim:

1. A liquid pharmaceutical composition comprising amoxicillin; clavulanic acid or a salt thereof; one or more of dried silicon dioxide, dried colloidal silicon dioxide and dried magnesium trisilicate; and a low moisture content medium chain triglyceride vehicle, wherein the composition is a liquid, the concentration of medium chain triglycerides ranges from about 50% to about 99% (w/v) of the composition, and the medium chain triglycerides contain less than about 1.0% (w/w) water.

2. The composition of claim 1, wherein the composition is a suspension.

3. The composition of claim 1, wherein the one or more of silicon dioxide, colloidal silicon dioxide and magnesium trisilicate are dried prior to inclusion in the pharmaceutical composition.

4. The composition of claim 3, wherein the one or more of silicon dioxide, colloidal silicon dioxide and magnesium trisilicate are dried by placing them in an oven at 105° C. overnight.

5. The composition of claim 4, wherein the medium chain triglyceride vehicle contains no more than about 0.0275% (w/w) water.

6. The composition of claim 1, comprising one or more of an antioxidant, an antibacterial agent, a preservative, a chelator, a coloring agent, a flavoring agent, and an emulsifier.

7. A liquid pharmaceutical suspension, consisting of:
   a) a powder comprising amoxicillin, potassium clavulanate and dried silicon dioxide; and
   b) a liquid consisting essentially of low moisture content medium chain triglycerides, wherein the medium chain triglycerides contain less than about 1.0% (w/w) water.

8. A method for preparing a pharmaceutical composition for reconstitution, comprising the steps of:
   a) drying one or more of silicon dioxide, colloidal silicon dioxide and magnesium trisilicate;
   b) mixing a β-lactam antibiotic, a β-lactamase inhibitor and the one or more of dried silicon dioxide, dried colloidal silicon dioxide and dried magnesium trisilicate to prepare a powder;
   c) placing an amount of the powder sufficient to provide a therapeutically effective amount of the β-lactam antibiotic into a first container;
   d) providing a second container containing a low moisture content medium chain triglyceride vehicle in a quantity sufficient to reconstitute the amount of the powder;
   e) packaging the first and second containers together in a kit.

9. The method of claim 8, wherein the powder comprises amoxicillin, potassium clavulanate and one or more of silicon dioxide, colloidal silicon dioxide and magnesium trisilicate.

10. The method of claim 8, wherein the step of drying the one or more of silicon dioxide, colloidal silicon dioxide and magnesium trisilicate comprises placing the one or more of silicon dioxide, colloidal silicon dioxide and magnesium trisilicate in an oven at 105° C. overnight.

11. A liquid pharmaceutical composition, comprising a β-lactam antibiotic, a β-lactamase inhibitor, one or more dried hygroscopic excipients and a low moisture content medium chain triglyceride vehicle, wherein the composition is a liquid and the medium chain triglyceride vehicle contains less than about 1.0% (w/w) water.

12. The composition of claim 11, wherein the composition is a suspension.

13. The composition of claim 11, wherein the β-lactam antibiotic is a penicillin selected from the group consisting of penicillin G, penicillin V, methicillin, nafcillin, oxacillin, cloxacillin, dicloxacillin, ampicillin, amoxicillin, carbenicillin, ticarcillin, piperacillin, mezlocillin, aziocillin, and mixtures thereof.

14. The composition of claim 11, wherein the β-lactam antibiotic is amoxicillin.

15. The composition of claim 11, wherein the β-lactamase inhibitor is clavulanic acid or a salt thereof.

16. The composition of claim 11, wherein the one or more hygroscopic excipients comprise silicon dioxide.

17. The composition of claim 11, wherein the one or more hygroscopic excipients comprise one or more of silicon dioxide, colloidal silicon dioxide and magnesium trisilicate.

18. The composition of claim 11, wherein the hygroscopic excipients are dried prior to inclusion in the pharmaceutical composition.

19. The composition of claim 18, wherein the hygroscopic excipients are dried by placing them in an oven at 105° C. overnight.

20. The composition of claim 18, wherein the medium chain triglyceride vehicle contains no more than about 0.0275% (w/w) water.

21. The composition of claim 11, wherein the concentration of medium chain triglycerides is from about 50% (w/v) to about 99% (w/v).

22. The composition of claim 11, wherein the β-lactam antibiotic is stable for at least about ten days when stored at a temperature of about 20° C. to about 25° C.

23. The composition of claim 1, wherein the medium chain triglycerides contain less than about 0.1% (w/w) water.

24. The composition of claim 1, wherein the composition is suitable for oral delivery.

25. The composition of claim 11, wherein the medium chain triglycerides contain less than about 0.1% (w/w) water.

26. The composition of claim 11, wherein the composition is suitable for oral delivery.

27. A liquid pharmaceutical composition for oral delivery consisting essentially of amoxicillin, clavulanic acid or a salt thereof, one or more of silicon dioxide, colloidal silicon dioxide and magnesium trisilicate, and a low moisture content medium chain triglyceride vehicle, wherein the composition is a liquid, the concentration of medium chain triglycerides ranges from about 50% to about 99% (w/v) of the composition, and the medium chain triglycerides contain less than about 1.0% (w/w) water.

* * * * *